United States Patent
Powell et al.

(10) Patent No.: US 8,552,226 B2
(45) Date of Patent: Oct. 8, 2013

(54) PROCESS FOR HEAT INTEGRATION FOR ETHANOL PRODUCTION AND PURIFICATION PROCESS

(75) Inventors: Nathan Kirk Powell, Waxahachie, TX (US); Samuel Roundy, League City, TX (US); Lincoln Sarager, Houston, TX (US); Murray Viard, Houston, TX (US); R. Jay Warner, Houston, TX (US); Gerald Gruesendorf, Rosharon, TX (US); Radmila Jevtic, Pasadena, TX (US); Victor J. Johnston, Houston, TX (US); Fred Ronald Olsson, Corpus Christi, TX (US)

(73) Assignee: Celanese International Corporation, Dallas, TX (US)

(*) Notice: Subject to any disclaimer, the term of this patent is extended or adjusted under 35 U.S.C. 154(b) by 462 days.

(21) Appl. No.: 12/986,008

(22) Filed: Jan. 6, 2011

(65) Prior Publication Data
US 2011/0190552 A1    Aug. 4, 2011

Related U.S. Application Data

(60) Provisional application No. 61/300,815, filed on Feb. 2, 2010, provisional application No. 61/332,696, filed on May 7, 2010, provisional application No. 61/332,699, filed on May 7, 2010.

(51) Int. Cl.
*C07C 29/149* (2006.01)

(52) U.S. Cl.
USPC .......................................................... 568/885

(58) Field of Classification Search
USPC .......................................................... 568/885
See application file for complete search history.

(56) References Cited

U.S. PATENT DOCUMENTS

| | | | |
|---|---|---|---|
| 2,649,407 A | 8/1953 | Harrison et al. | |
| 2,702,783 A | 2/1955 | Harrison et al. | |
| 2,744,939 A | 5/1956 | Kennel | |
| 2,882,244 A | 4/1959 | Milton | |
| 3,130,007 A | 4/1964 | Breck | |
| 3,408,267 A | 10/1968 | Miller et al. | |
| 3,445,345 A | 5/1969 | Katzen et al. | |
| 3,478,112 A | 11/1969 | Karl et al. | |
| 4,275,228 A | 6/1981 | Gruffaz et al. | |
| 4,306,942 A | 12/1981 | Brush et al. | |
| 4,317,918 A | 3/1982 | Takano et al. | |
| 4,319,058 A | 3/1982 | Kulprathipanja et al. | |
| 4,395,576 A | 7/1983 | Kwantes et al. | |
| 4,398,039 A | 8/1983 | Pesa et al. | |
| 4,421,939 A | 12/1983 | Kiff et al. | |
| 4,454,358 A | 6/1984 | Kummer et al. | |
| 4,465,854 A | 8/1984 | Pond et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,517,391 A | 5/1985 | Schuster et al. | |
| 4,541,897 A | 9/1985 | Sommer et al. | |
| 4,626,321 A | 12/1986 | Grethlein et al. | |
| 4,678,543 A | 7/1987 | Houben et al. | |
| 4,692,218 A | 9/1987 | Houben et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,842,693 A | 6/1989 | Wheldon | |
| 4,961,826 A | 10/1990 | Grethlein et al. | |
| 4,985,572 A | 1/1991 | Kitson et al. | |
| 4,990,655 A | 2/1991 | Kitson et al. | |
| 4,994,608 A | 2/1991 | Torrence et al. | |
| 5,001,259 A | 3/1991 | Smith et al. | |
| 5,026,908 A | 6/1991 | Smith et al. | |
| 5,035,776 A | 7/1991 | Knapp | |
| 5,061,671 A | 10/1991 | Kitson et al. | |
| 5,070,016 A | 12/1991 | Hallberg | |
| 5,124,004 A | 6/1992 | Grethlein et al. | |
| 5,144,068 A | 9/1992 | Smith et al. | |
| 5,149,680 A | 9/1992 | Kitson et al. | |
| 5,185,308 A | 2/1993 | Bartley et al. | |
| 5,215,902 A | 6/1993 | Tedder | |
| 5,233,099 A | 8/1993 | Tabata et al. | |
| 5,237,108 A | 8/1993 | Marraccini et al. | |
| 5,250,271 A | 10/1993 | Horizoe et al. | |
| 5,254,758 A | 10/1993 | Hiles et al. | |
| 5,449,440 A | 9/1995 | Rescalli et al. | |
| 5,565,068 A | 10/1996 | Parker et al. | |
| RE35,377 E | 11/1996 | Steinberg et al. | |
| 5,599,976 A | 2/1997 | Scates et al. | |
| 5,770,770 A | 6/1998 | Kim et al. | |
| 5,821,111 A | 10/1998 | Grady et al. | |

(Continued)

FOREIGN PATENT DOCUMENTS

| | | |
|---|---|---|
| WO | WO 83/03409 | 10/1983 |
| WO | WO 2007/003897 | 1/2007 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2009/105860 | 9/2009 |
| WO | WO 2010/055285 | 5/2010 |

OTHER PUBLICATIONS

International Search Report and Written Opinion for PCT/US2011/023305 dated Sep. 26, 2011 (10 pages).
Written Opinion for PCT/US2011/023305 mailed May 8, 2012.
International Preliminary Report on Patentability for PCT/US2011/023305 mailed Jun. 26, 2012.

*Primary Examiner* — Elvis O Price (57) ABSTRACT

Ethanol production from the hydrogenation of acetic acid requires energy to drive the hydrogenation reaction and the purification of the crude ethanol product. Heat integration process to recover heat from one part of the production process to be used within the process improves efficiencies and reduces costs.

30 Claims, 2 Drawing Sheets

(56) References Cited

U.S. PATENT DOCUMENTS

| | | |
|---|---|---|
| 6,121,498 A | 9/2000 | Tustin et al. |
| 6,143,930 A | 11/2000 | Singh et al. |
| 6,294,703 B1 | 9/2001 | Hara et al. |
| 6,375,807 B1 | 4/2002 | Nieuwoudt et al. |
| 6,509,180 B1 | 1/2003 | Verser et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,115,772 B2 | 10/2006 | Picard et al. |
| 7,208,624 B2 | 4/2007 | Scates et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,732,173 B2 | 6/2010 | Mairal et al. |
| 2006/0019360 A1 | 1/2006 | Verser et al. |
| 2007/0270511 A1 | 11/2007 | Melnichuk et al. |
| 2008/0135396 A1 | 6/2008 | Blum |
| 2009/0014313 A1 | 1/2009 | Lee et al. |
| 2009/0023192 A1 | 1/2009 | Verser et al. |
| 2009/0081749 A1 | 3/2009 | Verser et al. |
| 2009/0166172 A1 | 7/2009 | Casey et al. |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0197485 A1 | 8/2010 | Johnston et al. |
| 2011/0082322 A1 | 4/2011 | Jevtic et al. |

PROCESS FOR HEAT INTEGRATION FOR ETHANOL PRODUCTION AND PURIFICATION PROCESS

CROSS REFERENCE TO RELATED APPLICATIONS

This application claims priority to U.S. Provisional App. No. 61/300,815, filed on Feb. 2, 2010, U.S. Provisional App. No. 61/332,696, filed on May 7, 2010, and U.S. Provisional App. No. 61/332,699, filed on May 7, 2010, the entire contents and disclosures of which are incorporated herein by reference.

FIELD OF THE INVENTION

The present invention relates generally to processes for heat integration in the production of ethanol, and, in particular, heat integration in the production of ethanol from the hydrogenation of acetic acid.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol for fuels or consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

Conventional methods have been used for separating ethanol from fermentation processes. These methods have proposed various thermally-integrated configurations, such as those described in U.S. Pat. Nos. 5,215,902, 5,035,776, 4,626,321, and 4,306,942. However, these systems deal with different feed streams and separation requirements. Therefore, a need remains for improving the energy efficiency in the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, the process comprising the steps of introducing an acetic acid vapor feed stream comprising acetic acid into a first reactor hydrogenating the acetic acid in the first reactor in the presence of a first catalyst to form a first reactor product stream comprising ethanol and residual acetic acid. The process further comprises cooling the first reactor product stream in a first heat exchange stage, wherein the first reactor product stream is cooled to a temperature that is equal to or greater than a feed temperature to the first reactor. In addition, the process comprises hydrogenating the residual acetic acid in a second reactor in the presence of a second catalyst to form a second reactor product stream comprising ethanol; and cooling the second reactor product stream in a second heat exchange stage.

In a second embodiment, the present invention is directed to a process for producing ethanol, the process comprising the steps of hydrogenating acetic acid from an acetic acid vapor feed stream in a reactor in the presence of a catalyst to form a crude reactor product; flashing the crude reactor product to form a vapor stream and a liquid stream comprising ethanol, ethyl acetate, water, and acetic acid; and separating at least a portion of the liquid stream in a first distillation column to produce a first distillate comprising ethanol, ethyl acetate and water, and a first residue comprising acetic acid. The process may transfer heat of the first distillate in a first heat exchange stage. The process further comprises separating a condensed portion of the first distillate in a second distillation column to produce a second distillate comprising ethyl acetate and second residue comprising ethanol and water; and separating a portion of the second residue in a third distillation column to produce a third distillate comprising ethanol and third residue comprising water. The process may cool a portion of the third residue in a second heat exchange stage.

BRIEF DESCRIPTION OF DRAWINGS

The invention is described in detail below with reference to the appended drawings, wherein like numerals designate similar parts.

DETAILED DESCRIPTION OF THE INVENTION

The present invention relates to processes for recovering ethanol produced by hydrogenating acetic acid in the presence of a catalyst. Hydrogenation may also produce one or more byproducts that are separated in one or more distillation columns. The distillation columns require heat to separate the byproducts from ethanol. In addition, there are several feed streams that require heating before hydrogenation that also require cooling after the reaction. In particular, the present invention integrates heat within the process to improve energy efficiency. In one embodiment, the hydrogenation reactor operates in the vapor phase at a temperature higher than the purification system. Because the hydrogenation reactor produces a crude product in the vapor phase and the purification is in the liquid phase the heat of the reaction cannot be readily transferred directly by the crude product. Without transferring the heat through the crude product the system may lose heat and reduce the overall efficiency.

One embodiment of the present invention advantageously incorporates heat integration through one or more heat stages. A heat stage refers to changing the temperature of a first stream through indirect contact with a second stream, e.g., a cooler first stream is heated by a hotter second stream through indirect contact of the first and second streams. In some embodiments, a hotter stream may be cooled by transferring heat to a cooler stream. In other embodiments, a cooler stream may be heated through heat transferred by a hotter stream. Heat stages allow the efficient use of the heat produced or used in one part of the system, e.g., the hydrogenation reactor, to be retained within another part of the process. The heat stage may use any suitable indirect-contact heat exchangers, including direct transfer type heat exchangers or indirect transfer type heat exchangers, that are capable of transferring heat by conduction. In some embodiments, a heat transfer fluids, such as steam or oil, may transfer the heat from one stream to another stream. A preferred heat exchanger that may be used in embodiments of the present invention may be a spiral tube heat exchange, double-pipe heat exchanger, shell and tube heat exchanger, or fluidized-bed heat exchanger.

Figure 1:
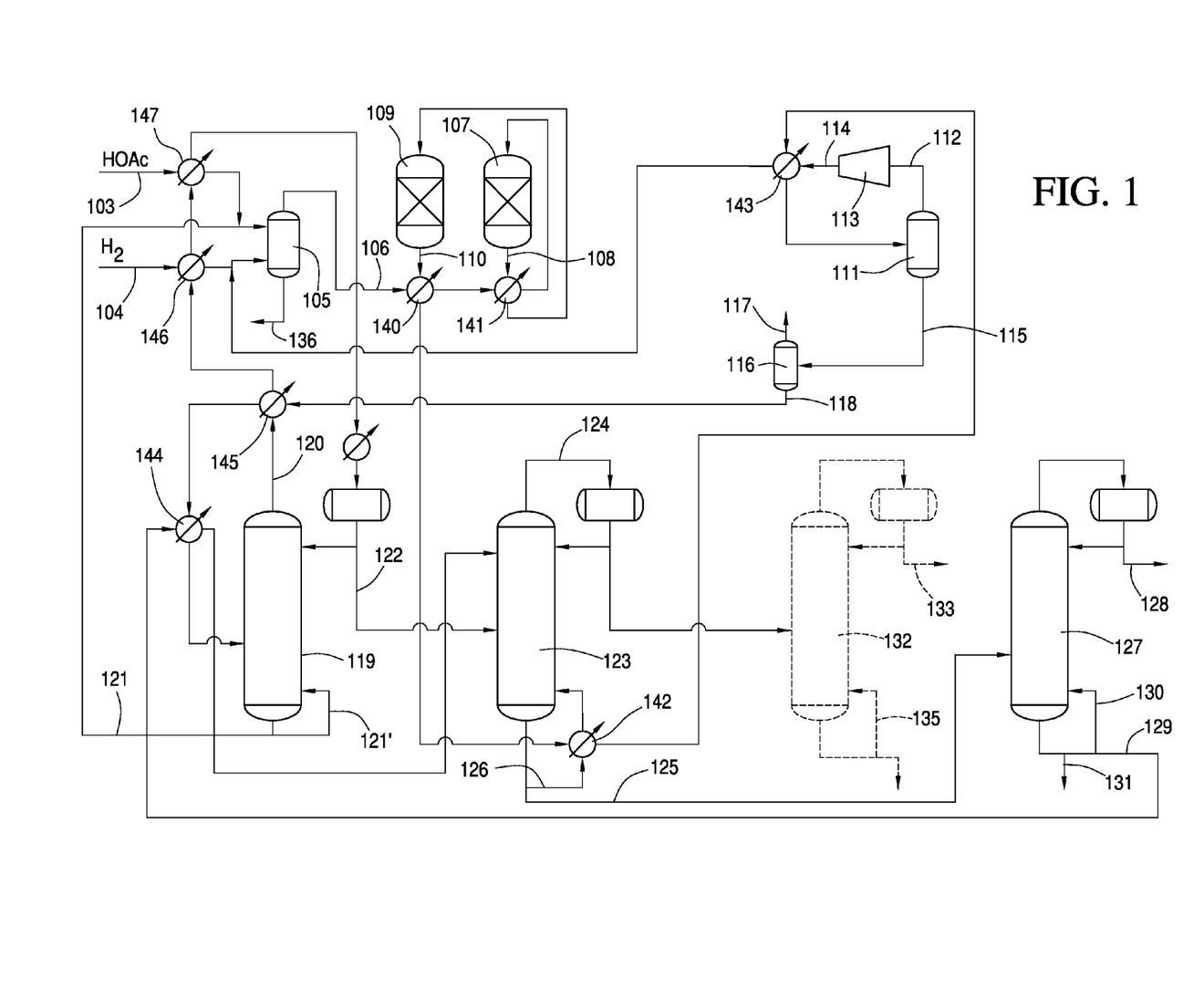
FIG. 1 is a schematic diagram of a hydrogenation system in accordance with one embodiment of the present invention.

FIG. 1 shows a hydrogenation system 100 suitable for the hydrogenation of acetic acid and separating ethanol from the crude reaction mixture according to one embodiment of the invention. System 100 comprises reaction zone 101 and distillation zone 102. Acetic acid and hydrogen are fed to a vaporizer 105 via lines 103 and 104, respectively, to create a vapor feed stream 106 comprising acetic acid and hydrogen that is directed to a first reactor 107 and/or second reactor 109.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, such a process can also be used to make hydrogen which may be utilized in connection with this invention.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the disclosure of which is incorporated herein by reference. Optionally, the production of ethanol may be heat integrated with such methanol carbonylation processes.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas as well as U.S. Pat. No. 6,685,754, the disclosures of which are incorporated herein by reference.

In one optional embodiment, the acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the present of carboxylic acids, such as propanoic acid or its anhydride, may be beneficial in producing propanol.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

In a preferred embodiment, hydrogen in feed line 104 may be preheated by a heat exchanger 146. Acetic acid in feed line 103 may also be preheated by a heat exchanger 147. Preferably, the heat exchangers 146 and 147 are integrated with a distillate stream from the distillation zone 102. The distillate stream 120 may be from the acetic acid removal column 119 that generally operates at a higher temperature than the other columns to remove heavier components from the crude ethanol product. In the heat exchange stage, the distillate stream 120 may transfer latent heat to acetic acid feed line 103, hydrogen feed line 104, or both, through indirect heat transfer in heat exchangers 146 and 147, respectively. Preferably distillate stream 120 may be condensed by heat exchangers 146 and 147, along with heat exchanger 145. In one embodiment, distillate stream 120 may remain in the vapor phase and may not be condensed until after transferring sensible heat to the feed lines 103 and 104. A utility exchanger may further condense distillate stream 120. Although FIG. 1 depicts heat exchangers 146 and 147 in series, heat exchangers 146 and 147, along with heat exchanger 145, may preferably be arranged in parallel.

In other embodiments, heat exchangers 146 and 147 may be heat integrated with another stream from within the hydrogenation system 101. Another suitable heat stage for heat exchangers 146 and/or 147 may involve transfer of heat from the effluent from one or more of the reactors. Also, a residue stream from one of the distillation columns, such as the acetic acid column 119 and/or product column 127 may also be heat integrated with heat exchangers 146 and/or 147. Preferably, heat exchangers 146 and 147 are heat integrated with the same stream so that each stream is preheated to a similar temperature. In one embodiment, acetic acid in feed line 103 may be preheated with the residue in line 121 from acetic acid column 119.

In further embodiments, one or more utility exchangers may be used to further preheat acetic acid and/or hydrogen in feed lines 103 and 104, respectively. Utility exchangers refer generically to exchangers that are not integrated with system 100 and receive heat or cooling from an outside source.

Preferably acetic acid in line 103 may be preheated to a temperature of at least 40° C., e.g., at least 70° C. or at least 85° C., prior to being fed to vaporizer 105. Hydrogen in line 104 preferably is preheated to a temperature of at least 40° C., e.g., at least 70° C. or at least 85° C., prior to being fed to vaporizer 105.

In one embodiment, lines 103 and 104 may be combined and jointly fed to vaporizer 105, e.g., in one stream containing both hydrogen and acetic acid. The acetic acid may be vaporized at the reaction temperature, and then fed via vapor feed stream 106 to first reactor 107. Vapor feed stream 106 may also comprise hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment the acetic acid may be vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor by passing hydrogen and/or recycle gas through the acetic acid at a temperature at or below 125° C., followed by heating of the combined gaseous stream to the reactor inlet temperature.

Any feed that is not vaporized is removed from vaporizer 105, as shown in FIG. 1 by blowdown stream 136, and may be recycled thereto. Optionally a portion of stream 136 may be fed to a reboiler that heats vaporizer 105.

The temperature of vapor feed stream 106 upon exiting vaporizer 105 is preferably from 100° C. to 250° C., e.g., from 105° C. to 200° C. or from 110° C. to 150° C. Preferably, vapor feed stream 106 may be preheated by one or more heat exchangers before being fed to first reactor 107. As shown by FIG. 1, vapor feed stream 106 may be preheated by heat exchangers 140 and/or 141. Heat exchangers 140 and/or 141 are integrated with the first reactor product 108 from first reactor 107 and the second reactor product 110 from second reactor 109. The first reactor product 108 and second reactor product 110 may be generically referred to as the crude reaction product and each has a composition as described below in Table 1. In one embodiment, the first reactor product 108 contains relatively more unreacted acetic acid than the second reactor product 110. It should be understood that some embodiments may use additional reactors and the effluent of those additional reactors may be heat integrated in a heat exchanger to preheat vapor feed stream 106. After pre-heating in heat exchangers 140 and 141, vapor feed stream 106 may have a temperature of greater than 120° C., e.g., greater than 150° C. or greater than 190° C. Preferably, vapor feed stream 106 is heated to a temperature below the reaction temperature in first reactor 107.

In preheating vapor feed stream, heat exchangers also cool first reactor product 108 and second reactor product 110 of first reactor 107 and second reactor 109, respectively. Due to the exothermic hydrogenation reactor, the first reactor product 108 and second reactor product 110 exit each reactor at or near the reaction temperature. Preferably, first reactor product 108 from first reactor 107 is cooled to a temperature that is greater than or equal to the feed temperature to first reactor 107. The temperature of the first reactor product 108 fed to second reactor 109 is preferably from 120° C. to 350° C., e.g., from 150° C. to 325° C. or from 200° C. to 275° C. Maintaining first reactor product 108 above the feed temperature reduces the need for further preheating before being fed to the second reactor 109. The second reactor product 110 may be cooled below the feed temperature through one or more heat exchange stages.

Vapor feed stream 106 may be directed to the top of first reactor 107, and first reactor product 108 may be directed to the top of second reactor 109, as shown in FIG. 1. First reactor 107 and second reactor 109 may each comprise one or more reactor beds. There may be heat integrated between the reactor beds and cooling of the streams between the reactor beds. Lines 106 and 108 may, in some embodiments, be directed to the side, upper portion, or bottom of either reactor 107 or 109. The hydrogenation reaction in the second reactor 109 preferably uses the unreacted acetic acid and hydrogen in line 108. Although fresh reactants may be fed to second reactor 109, it is preferred that second reactor 109 operates with the unreacted reactants, acetic acid and hydrogen, of the first reactor product 108.

In FIG. 1, prior to be purified or separated, second reactor product 110 may be further cooled in one or more heat exchange stages. Preferably, second reactor product 110 may be cooled in heat exchanger 141 with vapor feed stream 106 as discussed above. Because second reactor product 110 has a higher temperature than distillation zone 102, it is preferred to also cool second reactor product 110 with one or more heat exchange stages with streams from distillation zone 102. In addition, second reactor product 110 may also be cooled through a heat exchange with a reboiler stream on one of the distillation columns. As shown in FIG. 1, it is preferred to transfer heat to reboiler stream 126 of light ends column 123 through heat exchanger 142. In addition, as shown in FIG. 1, second reactor product 110 may be cooled in heat exchanger 143 with recycled compressed vapor stream 114. The order of the heat exchange stages for cooling second reactor product 110 may vary depending on the layout of the facility. In other embodiments, second reactor product 110 may be cooled by heating another stream, such as the acetic acid and/or hydrogen feed lines or the liquid feed stream to distillation zone 102.

In first and second reactors 107 and 109 the hydrogenation of acetic acid forms ethanol and water in equal molar ratio, along with one or more byproducts. Suitable hydrogenation catalysts include catalysts comprising a first metal and optionally one or more metals, on a catalyst support. The first and optional metals may be selected from Group IB, IIB, IIIB, IVB, VB, VIIB, VIIB, VIII transitional metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. No. 7,608,744 and U.S. Pub. Nos. 2010/0029995 and 2010/0197485, the entireties of which are incorporated herein by reference.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal preferably is present in an amount from 0.1 and 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 and 4 wt. %, e.g., from 0.1 to 3 wt. %, or from 0.1 to 2 wt. %.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

In the production of ethanol, the catalyst support may be modified with a support modifier that is either acidic or basic. Preferably, the support modifier is a modifier that has a low volatility or no volatility. Suitable basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. Preferably, the basic support modifier is a calcium silicate, and more preferably calcium metasilicate ($CaSiO_3$). If the support modifier comprises calcium metasilicate, it is preferred that at least a portion of the calcium metasilicate is in crystalline form.

Suitable acidic modifiers include those selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$.

A preferred silica support material is SS61138 High Surface Area (HSA) Silica Catalyst Carrier from Saint-Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 (Sud Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

As will be appreciated by those of ordinary skill in the art, support materials are selected such that the catalyst system is suitably active, selective and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744, U.S. Pub. Nos. 2010/0029995 and 2010/0197485, referred to above, the entireties of which are incorporated herein by reference.

In general the hydrogenation reactors, e.g., first reactor 107 and second reactor 109, may include a variety of configurations using a fixed bed reactor vessel or a fluidized bed reactor vessel, as one of skill in the art will readily appreciate. Preferably at least two reactor vessels are used. Each reactor vessel may have one or more reactor beds. In one embodiment each reactor vessel may have at least two reactor beds. Preferably at least four reactor beds are used in embodiments of the present invention to achieve high conversion of acetic acid. In many embodiments of the present invention, an "adiabatic" reactor can be used; that is, there is little or no need for internal plumbing through the reaction zone to add or remove heat. In other embodiments, radial flow reactor or reactors may be employed, or a series of reactors may be employed with or without heat exchange, quenching, or introduction of additional feed material. Alternatively, a shell and tube reactor provided with a heat transfer medium may be used.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$. When the reaction is carried out in multiple reactors, each reactor preferably operates at similar conditions.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not detectable. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 or at least 600. In terms of ranges, the productivity preferably is from 200 to 3,000 grams of ethanol per kilogram catalyst per hour, e.g., from 400 to 2,500 or from 600 to 2,000.

In various embodiments, the crude ethanol product produced by the hydrogenation process, before any subsequent processing, such as purification and separation, will typically comprise unreacted acetic acid, ethanol and water. As used herein, the term "crude ethanol product" generally refers to any composition comprising from 5 to 70 wt. % ethanol and from 5 to 35 wt. % water. Exemplary embodiments of crude ethanol compositional ranges are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In addition, multiple reactor vessels and/or reactor beds may be used that each preferably contain a similar hydrogenation catalyst. In one embodiment, a similar catalyst may be used in each of the reactors 107 and 109. Preferably, in each reactor the catalyst comprises similar metals, but the amounts of the metals on the catalyst may vary between the reactor vessels and/or reactor beds. In addition, the supports may also vary. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product is withdrawn, preferably continuously, from reactor 107 via line 108 and from reactor 109 via line 110. The crude ethanol product in line 110, after cooling through heat exchangers 141, 142 and 143, may be further condensed and fed to a high pressure flasher 111 that provides a vapor stream and a liquid stream. Flasher 111 in one embodiment preferably operates at a temperature of from 50° C. to 500° C., e.g., from 70° C. to 400° C. or from 100° C. to 350° C. In one embodiment, the pressure of flasher 111 preferably is from 50 KPa to 2000 KPa, e.g., from 75 KPa to 1500 KPa or from 100 to 1000 KPa.

Vapor stream 112 exiting flasher 111 may comprise hydrogen and hydrocarbons, which may be purged and/or returned to reaction zone 101. As shown in FIG. 1, the returned portion of vapor stream 112 passes through compressor 113. Compressed stream 114 may be preheated by heat exchanger 143 and fed to vaporizer 105. In optional embodiments, the compressed stream 114 may be preheated by heat exchanger 146 along with fresh hydrogen from feed line 104.

The liquid from flasher 111 is withdrawn via liquid stream 115 and fed to a low pressure flasher 116. Low pressure flasher 116 preferably operates at a pressure of from 0.1 KPa to 1000 KPa, e.g., from 0.1 KPa to 500 KPa or from 0.1 KPa to 100 KPa. In one embodiment, the pressure of flasher 116 preferably is at least 50 KPa lower than flasher 111, e.g., at least 100 KPa lower or at least 200 KPa lower. Flasher 116 may also operate at a lower temperature and/or pressure than flasher 111. In one embodiment, the temperature of flasher 116 preferably is from 20° C. to 100° C., e.g., from 30° C. to 85° C. or from 40° C. to 70° C. In one embodiment, the temperature of flasher 116 preferably is at least 50° C. lower than flasher 111, e.g., at least 75° C. lower or at least 100° C. lower.

The vapor stream 117 exiting flasher 116 may comprise hydrogen and hydrocarbons, and is preferably purged. Optionally, vapor stream 117 may be returned to the reaction zone 101 in a manner similar to that of vapor stream 112. The liquid feed stream 118 from flasher 116 is withdrawn and fed to first column 119.

In one embodiment, liquid feed stream 118 may be preheated in one or more heat exchange stages before being separated in first column 119. Preferably, liquid feed stream 118 is heated to a temperature from 50° C. to 180° C., e.g., 80° C. to 140° C. or from 100° C. to 120° C. Liquid feed stream 118 may be preheated in two heat exchange stages by heat exchangers 144 and 145. In heat exchanger 144 liquid feed stream 118 is indirectly heated by the third residue 129 from the third column 127, referred to as the product column. In heat exchanger 145 liquid feed stream 118 is indirectly heated by distillate stream 120 of first column 119. Preferably distillate stream 120 may be condensed by heat exchanger 145. In one embodiment, distillate stream 120 may remain in the vapor phase and may not be condensed until after transferring the heat to liquid feed stream 118. Although FIG. 1 depicts heat exchangers 145, 146, and 147 in series, heat exchangers 145, 146, and 147 may preferably be placed in parallel.

In some embodiments, low pressure flasher 116 may be bypassed, in part or in whole, and liquid stream 115 may be fed to distillation zone 102. When liquid stream 115 is fed to distillation zone, it is preferred to heat liquid stream in a manner similar to liquid feed stream 118, as described above.

The contents of stream 118, and stream 115, typically may be substantially similar to the product obtained directly from the reactor, and may, in fact, also be characterized as a crude ethanol product. However, liquid feed stream 118 preferably has substantially no hydrogen, carbon dioxide, methane or ethane, which are removed by flashers 111 and/or 116. Exemplary components of liquid feed stream 118, as well as liquid stream 115, are provided in Table 2. It should be understood that stream 115 and/or 118 may contain other components, not listed, such as components in the feed.

TABLE 2

FEED COMPOSITION

|  | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |

TABLE 2-continued

FEED COMPOSITION

|  | Conc. (wt. %) | Conc. (wt. %) | Conc. (wt. %) |
|---|---|---|---|
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 118, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

When the content of acetic acid in line 118 is less than 5 wt. %, the acid separation column 119 may be skipped and line 118 may be introduced directly to second column 123, also referred to herein as a light ends column.

In the embodiment shown in FIG. 1, line 118 is introduced in the lower part of first column 119, e.g., lower half or lower third. In first column 119, unreacted acetic acid, a portion of the water, and other heavy components, if present, are removed from the composition in line 118 and are withdrawn, preferably continuously, as residue. Some or all of the residue may be returned and/or recycled back to reaction zone 101 via line 121. A portion of the residue may be fed to a reboiler (not shown) via stream 121' to provide heat to column 119. The reboiler of column 119 may integrated with a suitable stream, such as first reactor product 108 and/or second reactor product 110.

First column 119 also forms an overhead distillate, which is withdrawn in line 120. Prior to condensing distillate stream 120, distillate may be directed to one or more heat exchange stages. The one or more heat stages may comprise heat exchangers arranged in parallel. As discussed above, it is preferred that distillate may be used to heat liquid feed stream 118 fed to column 119, acetic acid feed line 103 and hydrogen feed line 104. During these heat exchange stages, distillate stream 120 may be condensed to the liquid phase and refluxed to column 119, for example, at a ratio of from 10:1 to 1:10, e.g., from 3:1 to 1:3 or from 1:2 to 2:1.

Any of columns 119, 123, 127, or optional column 132 in distillation zone 102 may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIG. 1. As shown in FIG. 1, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. In addition to the reactors and flashers shown in FIG. 1, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 KPa to 3000 KPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependent on the composition of the material at that location and the pressure of column. In addition, feed rates may vary depending on the size of the production process and, if described, may be generically referred to in terms of feed weight ratios.

When first column 119 is operated under standard atmospheric pressure, the temperature of the first residue stream 121 preferably is from 95° C. to 120° C., e.g., from 105° C. to 117° C. or from 110° C. to 115° C. The temperature of the distillate stream 120 exiting from column 119 preferably is from 70° C. to 110° C., e.g., from 75° C. to 95° C. or from 80° C. to 90° C. In other embodiments, the pressure of first column 119 may range from 0.1 KPa to 510 KPa, e.g., from 1 KPa to 475 KPa or from 1 KPa to 375 KPa. Exemplary components of the distillate and residue compositions for first column 119 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| FIRST COLUMN | | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |

TABLE 3-continued

| FIRST COLUMN | | | |
|---|---|---|---|
| | Conc. (wt. %) | Conc. (wt. %) | Conc. (wt. %) |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

Depending on the reaction conditions, the crude ethanol product exiting reactors 107 and/or 109 in line 112 may comprise ethanol, acetic acid (unconverted), ethyl acetate, and water. After exiting reactors 107 and/or 109, a non-catalyzed equilibrium reaction may occur between the components contained in the crude ethanol product until it is added to flasher 111 and/or first column 119. This equilibrium reaction tends to drive the crude ethanol product to an equilibrium between ethanol/acetic acid and ethyl acetate/water.

In the event the crude ethanol product is temporarily stored, e.g., in a holding tank, prior to being directed to distillation zone 102, extended residence times may be encountered. Additional heat integration may be used to cool the crude ethanol product when stored in the holding tank and heat when withdrawn from the holding tank. Generally, the longer the residence time between reaction zone 101 and distillation zone 102, the greater the formation of ethyl acetate. For example, when the residence time between reaction zone 101 and distillation zone 102 is greater than 5 days, significantly more ethyl acetate may form at the expense of ethanol. Thus, shorter residence times between reaction zone 101 and distillation zone 102 are generally preferred in order to maximize the amount of ethanol formed. In one embodiment, a holding tank (not shown), is included between reaction zone 101 and distillation zone 102 for temporarily storing the liquid component from stream 115 and/or stream 118 for up to 5 days, e.g., up to 1 day, or up to 1 hour. In a preferred embodiment no tank is included and the condensed liquids are fed directly to the first distillation column 119. In addition, the rate at which the non-catalyzed reaction occurs may increase as the temperature of the crude ethanol product, e.g., in streams 115 and/or 118, increases. These reaction rates may be particularly problematic at temperatures exceeding 30° C., e.g., exceeding 40° C. or exceeding 50° C. Thus, in one embodiment, the temperature of liquid components in stream 115 or in the optional holding tank is maintained at a temperature less than 40° C., e.g., less than 30° C. or less than 20° C. One or more cooling devices may be used to reduce the temperature of the liquid in streams 115 and/or 118.

As discussed above, a holding tank (not shown) may be included between the reaction zone 101 and distillation zone 102 for temporarily storing some or all of the streams 115 and/or 118, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude ethanol product is increased. For example, as the temperature of the crude ethanol product in streams 115 and/or 118 increases from 4° C. to 21° C., the rate of ethyl acetate formation may increase from about 0.01 wt. % per hour to about 0.005 wt. % per hour. Thus, in one embodiment, the temperature of liquid components in streams 115 and/or 118 or in the optional holding tank is maintained at a temperature less than 21° C., e.g., less than 4° C. or less than −10° C. In one embodiment, after liquid in streams 115 and/or 118 is stored, it may be preheated in one or more heat exchange stages.

First distillate stream 120 preferably comprises ethanol, ethyl acetate, and water, along with other impurities, which may be difficult to separate due to the formation of binary and tertiary azeotropes. The condensed first distillate 122 is introduced to the second column 123, also referred to as the "light ends column," preferably in the middle part of column 123, e.g., middle half or middle third. As one example, when a 25 tray column is utilized in a column without water extraction, condensed first distillate 122 is introduced at tray 17. In one embodiment, the second column 123 may be an extractive distillation column. In such embodiments, an extraction agent, such as water, may be added to second column 123. An extraction agent may also be obtained from an external source. Preferably, third reside 129 which comprises water from the third column 127 may be used as the extractive agent. Prior to feeding the extraction agent to the second column 123, third residue 129 may be cooled in one or more heat exchange stages. Preferably, third residue 129 is cooled by indirectly heating liquid feed stream 118 in heat exchanger 144. Third residue 129 may also be cooled by indirectly heating a reboiler. Third residue 129 may be cooled to a temperature of from 35° C. to 100° C., e.g., 65° C. to 95° C. or from 75° C. to 85° C. Without cooling third residue 129, third residue 129 would tend to vaporize the feed to second column 123 and thus limiting extractive distillation.

Second column 123 may be a tray column or packed column. In one embodiment, second column 123 is a tray column having from 5 to 70 trays, e.g., from 15 to 50 trays or from 20 to 45 trays. Although the temperature and pressure of second column 123 may vary, when at atmospheric pressure the temperature of the second residue 124 preferably is from 60° C. to 90° C., e.g., from 70° C. to 90° C. or from 80° C. to 90° C. The temperature of the second distillate 125 preferably is from 50° C. to 90° C., e.g., from 60° C. to 80° C. or from 60° C. to 70° C. Column 123 may operate at atmospheric pressure. In other embodiments, the pressure of second column 123 may range from 0.1 KPa to 510 KPa, e.g., from 1 KPa to 475 KPa or from 1 KPa to 375 KPa. Exemplary components for the distillate and residue compositions for second column 123 are provided in Table 4 below. It should be understood that the distillate and residue may also contain other components, not listed, such as components in the feed.

TABLE 4

SECOND COLUMN

| | Conc. (wt. %) | Conc. (wt. %) | Conc. (wt. %) |
|---|---|---|---|
| Distillate | | | |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue | | | |
| Water | 30 to 70 | 30 to 60 | 30 to 50 |
| Ethanol | 20 to 75 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 123, the weight ratio of ethyl acetate in the second residue to ethyl acetate in the second distillate approaches zero.

A portion of the residue in line 125 may be heated in reboiler stream 126 through heat exchanger 142 to supply the energy for column 123. As discussed above, heat exchanger 142 preferably is integrated with the second reactor product 110. Optionally, heat exchanger 142 may also be heat integrated with other streams, such as the residue of another column, and in particular column 119 and/or column 127. Additional utility exchangers (not shown) may also be used to control start up conditions.

As shown, the second residue from the bottom of second column 123, which comprises ethanol and water, is fed via line 125 to third column 127, also referred to as the "product column." More preferably, the second residue in line 125 is introduced in the lower part of third column 127, e.g., lower half or lower third. Third column 127 recovers ethanol, which preferably is substantially pure other than the azeotropic water content, as the distillate stream 128. The distillate of third column 127 preferably is refluxed as shown in FIG. 1, for example, at a reflux ratio of from 1:10 to 10:1, e.g., from 1:3 to 3:1 or from 1:2 to 2:1. The third residue stream 129, which preferably comprises primarily water, preferably is removed from the system 100 or may be partially returned to any portion of the system 100. Third column 127 is preferably a tray column as described above and preferably operates at atmospheric pressure. The temperature of the third distillate exiting in line 128 from third column 127 preferably is from 60° C. to 110° C., e.g., from 70° C. to 100° C. or from 75° C. to 95° C. The temperature of the third residue 129 exiting from third column 127 preferably is from 70° C. to 115° C., e.g., from 80° C. to 110° C. or from 85° C. to 105° C., when the column is operated at atmospheric pressure. Exemplary components of the distillate and residue compositions for third column 127 are provided in Table 5 below. It should be understood that the distillate and residue may also contain other components, not listed, such as components in the feed.

TABLE 5

THIRD COLUMN

| | Conc. (wt. %) | Conc. (wt. %) | Conc. (wt. %) |
|---|---|---|---|
| Distillate | | | |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue | | | |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 119, 123 and/or 127 in the system 100. Preferably at least one side stream is used to remove impurities from the third column 127. The impurities may be purged and/or retained within the system 100.

The third residue 129 may be used as an extractive agent for column 123. When used as an extractive agent, it may be preferred to cool the third residue 129 in one or more heat exchange stages. Preferably, as discussed above, third residue 129 is cooled indirectly heating liquid feed stream 118 in heat exchanger 144. In addition, a portion of third residue 129 may be directed to a reboiler via stream 130. This portion in stream 130 may be heated in one or more heat exchange stages. Also, a portion of the third residue 129 may be purged from the system 100 via stream 131. Depending on the subsequent use of purge stream 131, the purge stream 131 may be cooled.

In optional embodiments, the third distillate in line 128 may be cooled by in a heat exchange stage with one or more cool streams. Third distillate 128 may optionally be cooled indirectly heating liquid feed stream 118 in a heat exchanger (not shown). Third distillate may also be cooled indirectly heating the acetic acid feed line 103 and/or hydrogen feed line 104 to vaporizer 105 in a heat exchanger (not shown).

The third distillate in line 128 may be further purified to form an anhydrous ethanol product stream, i.e., "finished anhydrous ethanol," using one or more additional separation systems, such as, for example, distillation columns (e.g., a finishing column) or molecular sieves.

In optional embodiments, distillate 121 of first column 119 may be heat integrated with a reboiler (not shown) of third column 127. When using this heat integration, first column 119 may operate at an elevated pressure.

Returning to second column 123, the second distillate preferably is refluxed as shown in FIG. 1, for example, at a reflux ratio of from 1:10 to 10:1, e.g., from 1:5 to 5:1 or from 1:3 to 3:1. In one embodiment second distillate 124 may be fed to reaction zone 101, and in particular vaporizer 105 and/or first reactor 107. Optional purges may be taken from second distillate 124 to remove build up of impurities.

In optional embodiments, the second distillate is fed via line 124 to optional fourth column 132, also referred to as the "acetaldehyde removal column." In fourth column 132 the second distillate is separated into a fourth distillate, which comprises acetaldehyde, in line 133 and a fourth residue, which comprises ethyl acetate, in line 134. The fourth distillate 133 preferably is refluxed at a reflux ratio of from 1:20 to 20:1, e.g., from 1:15 to 15:1 or from 1:10 to 10:1, and a portion of fourth distillate 133 may be returned to the reaction zone 101. For example, fourth distillate 133 may be combined with acetic acid feed line 103, added to vaporizer 105, or added directly to first reactor 107. Without being bound by theory, since acetaldehyde may be hydrogenated to form ethanol, the recycling of a stream that contains acetaldehyde to the reaction zone increases the yield of ethanol and decreases byproduct and waste generation. In another embodiment (not shown in the figure), the acetaldehyde may be collected and used, with or without further purification, to make useful products including but not limited to n-butanol, 1,3-butanediol, and/or crotonaldehyde and derivatives.

The fourth residue of fourth column 132 may be purged via line 134. A portion of fourth residue in line 134 may be directed to a reboiler stream 135. The fourth residue primarily comprises ethyl acetate and ethanol, which may be suitable for use as a solvent mixture or in the production of esters. Fourth residue 134 may be hydrolyzed and the hydrolyzed products may be directed within the system 100. In one preferred embodiment, the acetaldehyde is removed from the second distillate in fourth column 134 such that no detectable amount of acetaldehyde is present in the residue of column 134.

Optional fourth column 132 is preferably a tray column as described above and preferably operates above atmospheric pressure. In one embodiment, the pressure is from 120 KPa to 5,000 KPa, e.g., from 200 KPa to 4,500 KPa, or from 400 KPa to 3,000 KPa. In a preferred embodiment the fourth column 132 may operate at a pressure that is higher than the pressure of the other columns.

The temperature of the fourth distillate exiting in line 134 from fourth column 132 preferably is from 60° C. to 110° C., e.g., from 70° C. to 100° C. or from 75° C. to 95° C. The temperature of the residue exiting from fourth column 132 preferably is from 70° C. to 115° C., e.g., from 80° C. to 110° C. or from 85° C. to 110° C. Exemplary components of the distillate and residue compositions for fourth column 132 are provided in Table 6 below. It should be understood that the distillate and residue may also contain other components, not listed, such as components in the feed.

TABLE 6

FOURTH COLUMN

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

The finished ethanol composition obtained by the processes of the present invention preferably comprises from 75 to 96 wt. % ethanol, e.g., from 80 to 96 wt. % or from 85 to 96 wt. % ethanol, based on the total weight of the finished ethanol composition. Exemplary finished ethanol compositional ranges are provided below in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol is from 80 to 1,000 wppm, e.g., from 95 to 1,000 wppm, from 100 to 700 wppm, or from 150 to 500 wppm. In one embodiment, the finished ethanol composition preferably is substantially free of acetaldehyde and may comprise less than 8 wppm of acetaldehyde, e.g., less than 5 wppm or less than 1 wppm.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircrafts. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid or reacted with polyvinyl acetate. The finished ethanol composition may be dehydrated to produce ethylene. Any of known dehydration catalysts can be employed in to dehydrate ethanol, such as those described in U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

In order that the invention disclosed herein may be more efficiently understood, an example is provided below. The following example describe the various heat integration processes of the present invention.

Example

Figure 2:
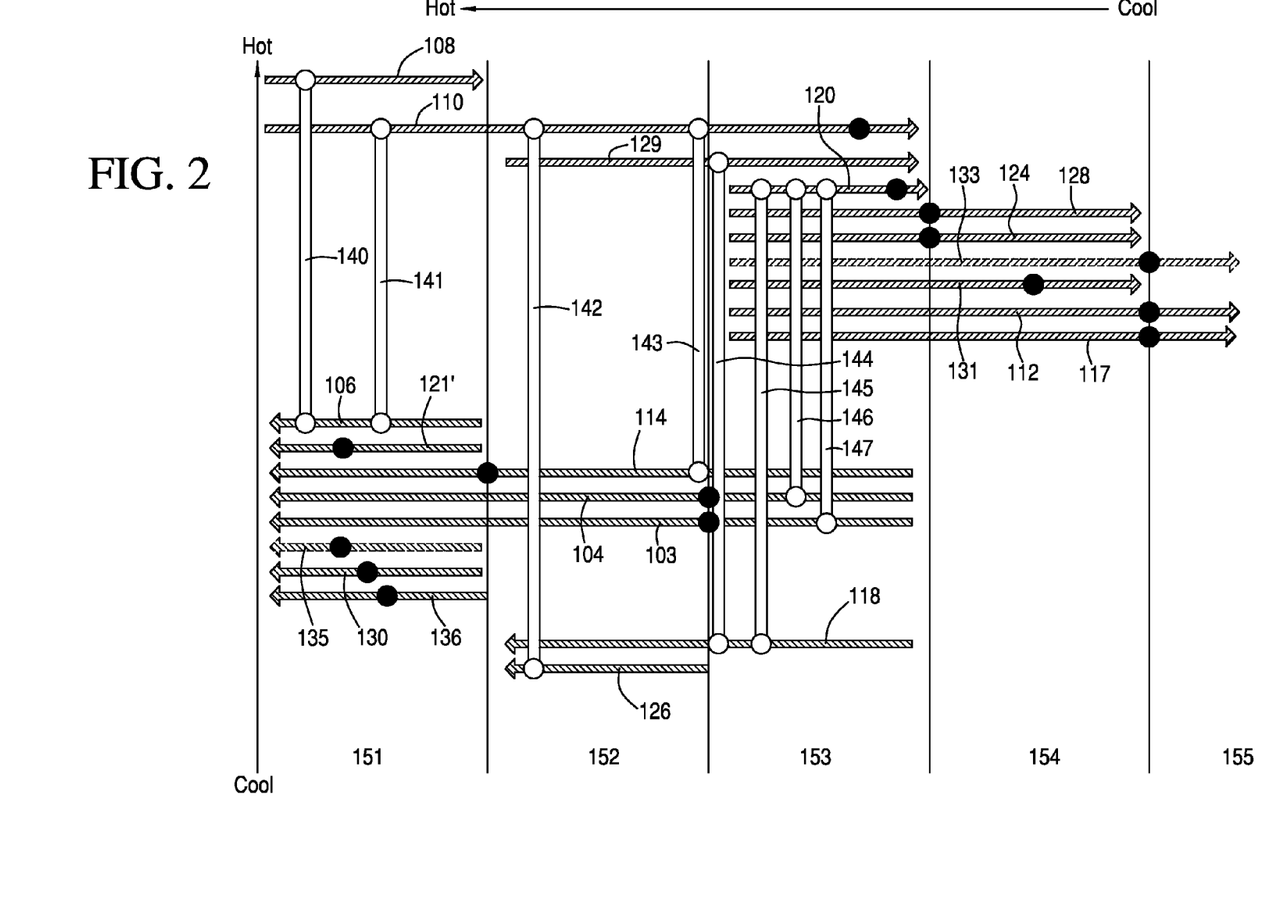
FIG. 2 is a thermodynamic model chart of heat integration for a hydrogenation system in accordance with one exemplary embodiment of the present invention.

A hydrogenation system, as constructed in FIG. 1, was thermodynamically modeled in FIG. 2 to integrate heat within the system. Each arrow represents a stream in the system that is either heated or cooled. In the thermodynamic model, there are five zones, 151-155, in which heat may be heat integrated between any of the hotter streams with the cooler streams.

In zone 151, two hot streams, first reactor product 108 and second reactor product 110, are cooled. Also there are several cool streams, vapor feed stream 106, reboiler stream 121', compressed vapor stream 114, acetic acid feed line 103, hydrogen feed line 104, reboiler stream 135, reboiler stream 130, and blowdown stream 136. First reactor product 108 exits first reactor 107 at a temperature of 292.3° C. and is cooled by heat exchanger 140 to a temperature of 250° C. Second reactor product 110 exits the second reactor 109 at a temperature of 279.5° C. and is cooled by heat exchanger 141 to a temperature of 141.4° C. Second reactor product 110 is subsequently cooled in zones 152 and 153. Heat exchangers 140 and 141 in turn heats vapor feed stream 106, from an initial temperature of 119.6° C. to 250° C.

As indicated by zone 151, additional heat integration of first reactor product 108 and second reactor product 110 with the other streams may be employed depending on the operating conditions of the system. In particular, the utility exchangers may be replaced by one or more heat exchange stages. For example, first reactor product 108 and/or second reactor product 110 may be heat integrated with reboiler streams 121', 135, and/or 130, as well as with blowdown stream 136.

In zone 152, there are two hot streams, second reactor product 110 and third residue 129. Also there are several cool streams, compressed vapor stream 114, acetic acid feed line 103, hydrogen feed line 104, reboiler stream 126, and liquid feed stream 118. Second reactor product 110 from zone 151 has a temperature of 141.4° C. and is cooled by heat exchanger 142 to a temperature of 115.6° C. Heat exchangers 142 heats reboiler stream 126 to temperature of about 103.8° C. Subsequently, second reactor product 110 may be further cooled by heat exchanger 143 to a temperature of 102.8° C. Heat exchanger 143 heats compressed vapor stream 114 from a temperature of 48.6° C. to 104.4° C. Compressed vapor stream 114 may further be heated by a utility exchanger in zone 151. Third residue may also be cooled to a temperature of 80° C. by heat exchanger 144. Heat exchanger 144 heats liquid feed stream 118 from a temperature of 67.8° C. to 110° C. Liquid feed stream 118 is also preheated in zone 153 by a heat exchanger 145.

In zone 153, in addition to hot streams second reactor product 110 and third residue 129 from zone 151, there are several other hot streams from the distillate streams of the columns. These hot streams include the first distillate 120, third distillate 128, second distillate 124, and optional fourth distillate 133. In addition, hot streams in zone 153 comprise vapor streams 112 and 117. The cool streams comprise compressed vapor stream 114, acetic acid feed line 103, hydrogen feed line 104, and liquid feed stream 118. First distillate 120 is used to transfer heat through heat exchangers 145, 146, and 147. First distillate 120 exits first column 119 at a temperature of about 96° C. may be transfer heat in heat exchangers 145, 146, and 147. First distillate 120 may also be subsequently condensed. Heat exchanger 145 heats liquid feed stream 118 from a temperature of 53.3° C. to 67.8° C. and liquid is subsequently heated by heat exchanger 144. Heat exchangers 146 and 147 heats hydrogen feed line 104 and acetic acid feed line 103, respectively, from a temperature of 32.2° C. to 85° C. Hydrogen feed line 104 and acetic acid feed line 103 are further heated by one or more utility exchangers in zones 151 and 152 prior to be introduced to vaporizer 105.

Although not used in this example, the other distillate streams may also be heat integrated in a similar manner as first distillate stream 120.

In zones 154 and 155 there are no cool streams shown in FIG. 2. However, these zones may be candidates for heat integration when colder hot streams are present. This may include intermediate storage where temperature may be very low. It is also a possible to heat integrate with scrubbers that require using a large amount of process water at a low temperature.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, the process comprising the steps of:
introducing an acetic acid vapor feed stream comprising acetic acid into a first reactor;
hydrogenating the acetic acid in the first reactor in the presence of a first catalyst to form a first reactor product stream comprising ethanol and residual acetic acid;
cooling the first reactor product stream in a first heat exchange stage, wherein the first reactor product stream is cooled to a temperature that is equal to or greater than a feed temperature to the first reactor;
hydrogenating the residual acetic acid in a second reactor in the presence of a second catalyst to form a second reactor product stream comprising ethanol; and
cooling the second reactor product stream in a second heat exchange stage.

2. The process of claim 1, wherein the first heat exchange stage further comprises heating the acetic acid vapor feed stream prior to being introduced to the first reactor.

3. The process of claim 1, wherein the first heat exchange stage further comprises heating a reboiler stream of a distillation column.

4. The process of claim 1, wherein the second heat exchange stage further comprises heating the acetic acid vapor feed stream prior to being introduced to the first reactor.

5. The process of claim 1, wherein the second heat exchange stage further comprises heating a reboiler stream of a distillation column.

6. The process of claim 1, further comprising introducing an acetic acid feed stream and a hydrogen feed stream to a vaporizer to produce the acetic acid vapor feed stream.

7. The process of claim 6, wherein the first heat exchange stage further comprises heating the acetic acid feed stream.

8. The process of claim 6, wherein the second heat exchange stage further comprises heating the acetic acid feed stream.

9. The process of claim 6, wherein the first heat exchange stage further comprises heating the hydrogen feed stream.

10. The process of claim 6, wherein the second heat exchange stage further comprises heating the hydrogen feed stream.

11. The process of claim 1, further comprising separating at least a portion of the second reactor product in a flasher into a vapor stream and a liquid stream.

12. The process of claim 11, wherein a portion of the vapor stream is directly or indirectly recycled as a recycle vapor stream to the first reactor and the second heat exchange stage further comprises heating the recycle vapor stream.

13. The process of claim 11, further comprising separating at least a portion of the liquid stream in one or more distillation columns.

14. The process of claim 13, wherein the first heat exchange stage further comprises heating the at least a portion of the liquid stream prior to being introduced to the one or more distillation columns.

15. The process of claim 1, wherein the second reactor product is cooled to a temperature that is less than the feed temperature to the first reactor.

16. The process of claim 1, wherein the first and second reactors each independently comprise one or more reactor beds.

17. A process for producing ethanol, the process comprising the steps of:
hydrogenating acetic acid from an acetic acid vapor feed stream in a reactor in the presence of a catalyst to form a crude reactor product;
flashing the crude reactor product to form a vapor stream and a liquid stream comprising ethanol, ethyl acetate, water, and acetic acid;
separating at least a portion of the liquid stream in a first distillation column to produce a first distillate comprising ethanol, ethyl acetate and water, and a first residue comprising acetic acid;
transferring heat of the first distillate in a first heat exchange stage;
separating a condensed portion of the first distillate in a second distillation column to produce a second distillate comprising ethyl acetate and second residue comprising ethanol and water;
separating a portion of the second residue in a third distillation column to produce a third distillate comprising ethanol and third residue comprising water; and
cooling a portion of the third residue in a second heat exchange stage.

18. The process of claim 17, wherein the first heat exchange stage further comprises heating the at least a portion of the liquid stream prior to being introduced to the first distillation column.

19. The process of claim 17, wherein the second heat exchange stage further comprises heating the at least a portion of the liquid stream prior to being introduced to the first distillation column.

20. The process of claim 17, further comprising feeding the cooled portion of the third residue to the second column.

21. The process of claim 17, transferring heat of the second distillate in a third heat exchange stage.

22. The process of claim 21, wherein the third heat exchange stage further comprises heating the at least a portion of the liquid stream prior to being introduced to the first distillation column.

23. The process of claim 17, further comprising introducing an acetic acid feed stream and a hydrogen feed stream to a vaporizer to produce the acetic acid vapor feed stream.

24. The process of claim 23, wherein the first heat exchange stage further comprises heating the acetic acid feed stream.

25. The process of claim 23, wherein the first heat exchange stage further comprises heating the hydrogen feed stream.

26. The process of claim 23, wherein the first heat exchange stage further comprises heating the acetic acid feed stream and the hydrogen feed stream in parallel.

27. The process of claim 23, wherein the second heat exchange stage further comprises heating the acetic acid feed stream and/or hydrogen feed stream.

28. The process of claim 23, transferring heat of the third distillate in a fourth heat exchange stage.

29. The process of claim 28, wherein the fourth heat exchange stage further comprises heating the at least a portion of the liquid stream prior to being introduced to the first distillation column.

30. The process of claim 28, wherein the fourth heat exchange stage further comprises heating the acetic acid feed stream and/or hydrogen feed stream.

* * * * *